United States Patent [19]

Kordomenos et al.

[11] Patent Number: 4,491,663

[45] Date of Patent: Jan. 1, 1985

[54] TRIFUNCTIONAL BLOCKED ISOCYANATE CONTAINING AN ISOCYANURATE RING

[75] Inventors: Panagiotis I. Kordomenos, Mt. Clemens; Andrew H. Dervan, Fraser, both of Mich.

[73] Assignee: Ford Motor Company, Dearborn, Mich.

[21] Appl. No.: 614,719

[22] Filed: May 29, 1984

Related U.S. Application Data

[63] Continuation of Ser. No. 368,178, Apr. 14, 1982, abandoned.

[51] Int. Cl.$^3$ .......................................... C07D 251/34
[52] U.S. Cl. ................................................... 544/193
[58] Field of Search ......................................... 544/193

[56] References Cited

U.S. PATENT DOCUMENTS

| | | | |
|---|---|---|---|
| 3,799,854 | 3/1974 | Jerabek | 204/181 |
| 4,080,345 | 3/1978 | Riemhofer | 260/2.5 AC |
| 4,195,146 | 3/1980 | Markiewitz et al. | 526/261 |
| 4,198,505 | 4/1980 | Frisch et al. | 544/221 |
| 4,265,798 | 5/1981 | Mishra | 260/32.4 |
| 4,288,586 | 9/1981 | Bock et al. | 528/67 |
| 4,302,351 | 11/1981 | Gras et al. | 252/182 |

*Primary Examiner*—John M. Ford
*Attorney, Agent, or Firm*—Roger L. May; Keith L. Zerschling

[57] ABSTRACT

Novel trifunctinal blocked isocyanates containing an isocyanurate ring and method of preparing are disclosed. Use of blocked isocyanates of invention as crosslinker for aqueous and nonaqueous compositions is also taught.

13 Claims, No Drawings

TRIFUNCTIONAL BLOCKED ISOCYANATE CONTAINING AN ISOCYANURATE RING

This application is a continuation, of application Ser. No. 368,178, filed Apr. 14, 1982 now abandoned.

BACKGROUND OF THE INVENTION

This invention relates to novel trifunctional blocked isocyanates containing an isocyanurate ring and to compositions containing same. More particularly, the invention relates to both solvent based and aqueous coating compositions including the novel trifunctional blocked isocyanate compound as a crosslinking agent. Still more particularly, the invention relates to such compositions which are capable of being exposed to higher temperatures without resulting in premature crosslinking, thus resulting in compositions with a better shelf stability and more desirable high temperature curing characteristics.

It is known to prepare isocyanurate containing isocyanates by cyclotrimerization of difunctional isocyanates. See for example A. A. S. Sayigh, Advances in Urethane Science and Technology, Volume 3 (1974), p. 141 and S. A. Fischer and W. H. Snyder, Organic Coatings and Plastics Chemistry, Volume 45 (1981), p. 36. Such a cyclotrimerization of difunctional isocyanates occurs in accordance with the following equation:

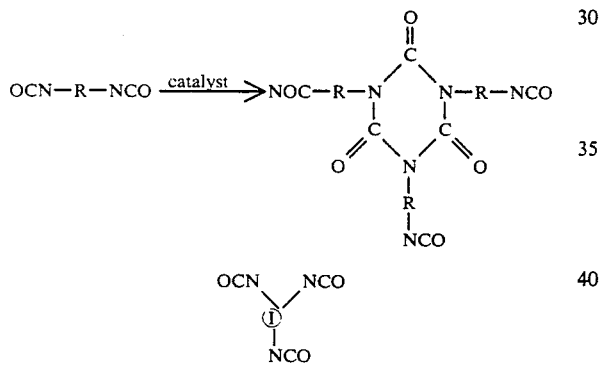

Where ① is an isocyanurate ring. Usually the reaction does not stop at the stage where there exists a pure trifunctional product as above, but continues through the formation of polyfunctional oligomers of the following type:

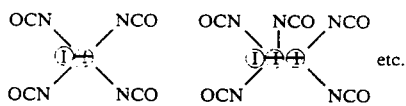

In view of the above, in order to obtain a pure trifunctional material it would be necessary to interupt the reaction at certain conversion levels and deactivate the catalyst employed. This is extremely difficult, if not impossible, to achieve and results at best in a mixture of the pure trifunctional material along with other oligomeric type reaction products.

A still further difficulty with the above method of preparing isocyanurate ring containing compounds is encountered in those cases where the diisocyanates to be trimerized are those in which one of the isocyanate groups has a reactivity greater than the other. Obviously, if the material is to be employed as a crosslinking agent, it is desirable to have the most reactive isocyanate groups available for the crosslinking reaction. However, when trimerizing this type of material, it trimerizes through the most reactive isocyanate group, thus resulting in a isocyanate functional product of significantly lower reactivity inasmuch as the isocyanates of lesser reactivity are those remaining after the trimerization. Thus, for example when toluene diisocyanate is trimerized in accordance with the teachings of the prior art, as depicted in the following formula, the isocyanate group in the para position reacts during the trimerization reaction, thus leaving the ortho isocyanate group available for the crosslinking reaction.

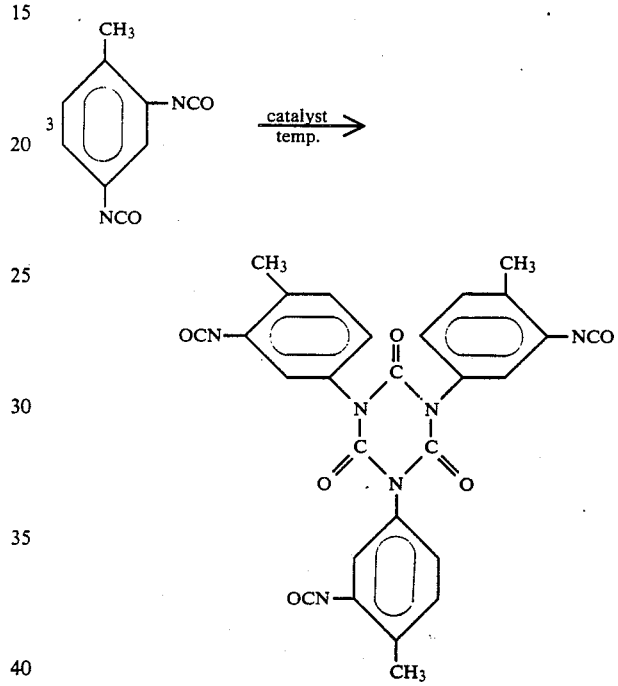

It has been found that by utilizing a blocking reaction and a subsequent cyclotrimerization reaction, that it is possible to prepare pure trifunctional polyisocyanate crosslinking agents containing isocyanurate ring.

SUMMARY OF THE INVENTION

The trifunctional blocked isocyanate compound of the invention contains an isocyanurate ring and has the formula

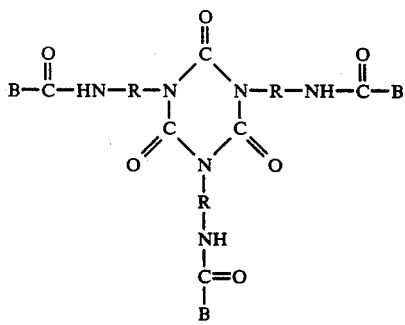

wherein R is selected from the group consisting of aliphatic, cycloaliphatic and aromatic groups and combinations thereof and B is the residue of an active hydrogen containing blocking agent. The compound of the invention is formed by (A) reacting (i) organic diisocyanate represented by the formula OCN—R—NCO and wherein one of the isocyanate groups thereof is more reactive than the other and (ii) sufficient active hydrogen containing blocking agent represented by the formula BH to react substantially all of the more reactive isocyanate groups; and (B) cotrimerizing the reaction product of (A) in the presence of a catalyst such that the isocyanurate ring containing compound is formed by the reaction of 3 moles of the blocked diisocyanate.

This novel trifunctional blocked isocyanate compound is useful as a crosslinking agent and has particular utility in situations where a higher temperature resistant coating is needed. While the compound is useful as a crosslinking agent in both aqueous and non-aqueous coating compositions, it is particularly useful in organic solvent based coating compositions, such as solvent based primer and topcoat compositions.

Preparation of the novel trifunctional blocked isocyanate compound and its use in both aqueous and non-aqueous coating compositions will be more fully understood from the following detailed description of the invention.

DETAILED DESCRIPTION OF THE INVENTION

Preparation of the Trifunctional Blocked Isocyanate Compound

As indicated above, the trifunctional blocked isocyanate compound of the invention contains an isocyanurate ring and has the formula

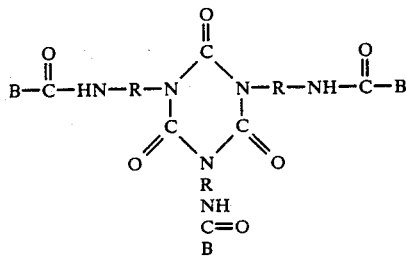

wherein R is selected from the group consisting of aliphatic, cycloaliphatic and aromatic groups and combinations thereof and B is the residue of an active hydrogen containing blocking agent. More specifically, the compound is formed by (A) reacting (i) organic diisocyanate represented by the formula OCN—R—NCO wherein one of the isocyanate groups is more reactive than the other and (ii) sufficient active hydrogen containing blocking agent represented by the formula BH to react substantially all of the more reactive isocyanate groups; and (B) cotrimerizing the reaction product of (A) in the presence of a catalyst such that the isocyanurate ring containing compound is formed by the reaction of 3 moles of the blocked diisocyanate.

The organic diisocyanates employed in the preparation of the crosslinking agent may be selected, as indicated above, from the group consisting of aliphatic, cycloaliphatic and aromatic diisocyanates and hybrids of those diisocyanates, provided that any of the diisocyanates selected, as also noted above, must have one isocyanate group which is more reactive than the other.

Numerous such diisocyanates will be apparent to those skilled in the art; representative of those organic diisocyanates which are suitable for use in the preparation of the trifunctional isocyanate crosslinking agents of the invention are 1-isocyanato-1(p-phenyl isocyanate)methane; 1-isocyanato-2(p-phenyl isocyanato)ethane; 4,4'-diisocyanato-2-nitro-biphenyl; and diisocyanates having either the formula

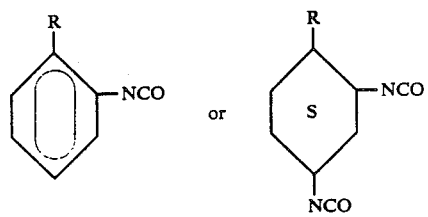

wherein R is selected from the group consisting of methyl, ethyl, t-butyl, chloro, bromomethyl, ethoxy, iso-butoxy, isopropyl, trichloromethyl and methoxy. Particularly preferred organic diisocyanates for use in preparation of the novel crosslinking compound of the invention are toluene diisocyanate and isophorone diisocyanate.

The active hydrogen containing blocking agents which are reacted with the above described organic diisocyanates may be selected from numerous blocking agents which will be apparent to those skilled in this art. Representative of those blocking agents which are preferred are those selected from the group consisting of (i) aliphatic, cycloaliphatic and aromatic alkyl monoalcohols, (ii) hydroxyl amines; (iii) oximes, (iv) lactams and (v) triazoles. Any suitable aliphatic, cycloaliphatic or aromatic alkyl monoalcohol may be used as a blocking agent in accordance with the present invention. For example, aliphatic alcohols, such as methyl, ethyl, chloroethyl, propyl, butyl, amyl, hexyl, heptyl, octyl, nonyl, 3,3,5-trimethylhexanol, decyl, and lauryl alcohols, and the like may be employed. Suitable cycloaliphatic alcohols include, for example, cyclopentanol, cyclohexanol and the like, while aromatic-alkyl alcohols include phenylcarbinol, methylphenylcarbinol, and the like. Minor amounts of even higher molecular weight relatively non-volatile monoalcohols may be used, if desired, to serve as plasticizers in the coatings provided by the invention. Examples of hydroxyl amines which may be employed as blocking agents include ethanol amine and propanol amine. Suitable oxime blocking agents include, for example, methylethylketone oxime, acetone oxime and cyclohexanone oxime. Examples of lactams which may be used as blocking agents are ε-caprolactam, γ-butyrolactam and pyrrolidone, while suitable triazoles include compounds such as 1,2,4 triazole, 1,2,3 benzotriazole, 1,2,3 tolyl triazole and 4,5 diphenyl-1,2,3 triazole. Particularly preferred active hydrogen containing blocking agents are methylethyl ketoxime and 2-ethylhexanol.

The intermediate blocked isocyanate reactant is formed by reacting a sufficient quantity of the blocking agent with the organic diisocyanate to insure that substantially all of the more reactive isocyanate groups of the organic diisocyanate reactant are reacted. This may be determined by NCO group titration. Generally, it is desirable to employ the organic diisocyanate and the active hydrogen containing blocking agent in a molar ratio of about 1:1.

After forming the above partially blocked organic diisocyanate intermediate, that intermediate is cotrimerized to form the pure trifunctional isocyanurate ring containing blocked isocyanate compound characterized by the above formula. Generally, the cotrimerizing of the reaction product takes place by trimerization of three moles of blocked diisocyanate reaction product to form one mole of the trimerized product.

In accordance with the invention water any light liquid organic substances may be used as the reaction medium provided that the substance has no functionality capable of reacting with an isocyanate group. Examples of such organic reaction medium liquids include, for example, acetone, ethylacetate, and halogen-substituted alkanes such as, for instance, methylene chloride, chloroform, ethylidene chloride, vinylidene chloride, monofluorotrichloromethane, chlorodifluoromethane, dichlorodifluoromethane and the like. Other suitable solvents include xylene, cellosolve acetate, toluene, etc. Still other suitable solvents will be apparent to those skilled in the art.

In accordance with the invention, there are further employed amine catalysts which are known to the art, such as, for example, tertiary amines such as triethylamine, tributylamine, N-methylmorpholine, N-ethylmorpholine, N-cocomorpholine, N,N,N',N'-tetramethylethylenediamine,1,4-diazabicyclo-(2,2,2)-octane N-methyl-N'-dimethylaminoethylpiperazine, N,N-dimethylbenzylamino, bis-(N,N-diethylaminoethyl)-adipate, N,N-diethylbenzylamine, pentamethyldiethylenetriamine, N,N-dimethylcyclohexylamine, N,N,N',N'-tetramethyl-1,3-butanediamine, N,N-dimethyl-beta-phenylethylamine, 1,2-dimethylimidazol, 2-methylimidazol and the like.

Tertiary amines having active hydrogen atoms for opposing isocyanate groups are for example illustrated by triethanolamine, N-ethyldiethanolamine, N-N-dimethylethanolamine as well as their reaction products with alkylene oxides, such as propylene oxide and/or ethylene oxide.

Other amine catalysts, include silaamines having —C—Si bonds such as those described in German Pat. No. 1,229,290. These include, for example, 2,2,4-trimethyl-2-silamorpholine, 1,3-diethylaminomethyltetramethyl-disiloxane and the like.

Metal compounds and, in particular, organic tin compounds can also be used as catalysts. Suitable organic tin compounds, include tin (II) salts of carboxylic acids, such as tin(II)-acetate, tin(II)-octoate, tin(II)-ethylhexoate and tin(II)-laurate and the dialkyl tin salts of carboxylic acids such as dibutyltin diacetate, dibutyl-tin diluaurate, dibutyl-tin maleate or dioctyl-tin diacetate.

Further instances of suitable catalysts are described in detail in Kunstoff-Handbuch, Vol, VII, Vieweg and Hochtlen, Carl Hanser Verlag, Munchen, 1966, at pp. 96–102.

The actual synthesis of the trifunctional isocyanurate ring containing blocked polyisocyanate crosslinking agent is carried out in two stages. In the first stage the blocking agents are reacted selectively with the more reactive isocyanate group at low temperature, for example, below 50° C. In the second stage the half-blocked isocyanate is cyclotrimerized at a temperature in the range of generally 80° C.–125° C. using a catalyst such as one of those listed above (e.g., potassium octoate) to form the isocyanurate crosslinker.

The novel trifunctional blocked isocyanate compounds of the invention, as noted above, may be used as crosslinking agents in numerous aqueous and nonaqueous coating compositions which will be apparent to those skilled in the art.

When the blocking agents are cyclic compounds such as ε-caprolactam, benzotriazole and cyclic amidines the disclosed crosslinkers may be used even in powder coating compositions such as those described in U.S. Pat. No. 4,255,551.

Among the aqueous compositions in which the crosslinker of the invention may be employed are electrodepositable compositions, particularly cationic systems wherein a film forming resin is deposited on the cathode. Blocked isocyanates have been used quite extensively as crosslinking agents in aqueous coating compositions, particularly in the above mentioned cationic electrodeposition systems. Exemplary of the numerous patents teaching the use of blocked isocyanate crosslinking agents are U.S. Pat. Nos. 3,799,854; 3,935,087; 4,031,050; 4,036,795 and 4,134.865. Typically, in accordance with these types of compositions the blocked crosslinking agent is mixed with a hydroxyl or amine functional polymer and then codispersed in a water/acid solution. It will be appreciated that the above compositions are only representative of the many aqueous compositions in which the crosslinker of the invention may be employed.

As noted above, the crosslinker of the invention is particularly useful in organic solvent based coating compositions, such as solvent based and topcoat compositions.

Compositions in which the crosslinker may be employed will be more apparent from the following examples which are merely intended to be representative.

EXAMPLE I

A first crosslinker in accordance with the invention was prepared as follows. Three (3) moles of 2,4 tolylene diisocyanate was weighed into a 2-liter round bottom flask equipped with a stirrer, reflux condensor, thermometer and heating mantel and 2-ethylhexanol (3 moles) was added dropwise over 40 minutes. The reaction temperature was held below 50° C. using a cold water bath and throughout the reaction the flask was flushed with dry nitrogen to maintain an inert atmosphere. After 2 hours the conversion, which was determined by measuring the isocyanate concentration by titration with dibutylamine solution was 49.7%. Five (5) grams of potassium octoate (0.55% on solids) was added to the flask. An exothermic reaction took place and 500 grams cellosolve acetate were added to stop the exothermic reaction at 125° C. The temperature dropped and held at 105° C. After two hours the trimer conversion was 98% and the reaction was terminated. The crosslinker was purified by repeated recrystallzation using cellosolve acetate and heptane.

EXAMPLE II 2,4 tolylene diisocyanate (2.0 moles) was weighed into a round bottom flask equipped as in Example I and methyl ethyl ketoxime (2.0 moles) was added dropwise over thirty minutes. The temperature was held below 45° C. and the flash flushed with nitrogen. After one hour the NCO conversion was 49.5%. The mixture was heated to 65° C. and 0.8 grams of potassium octoate (0.15% on solids) was dissolved in 50 grams xylene and added dropwise to the reaction mixture. After thirty minutes the temperature rose to 85° C. and an additional 80 grams of xylene were added. After one hour the NCO conversion was 91.3%. 0.3 grams of potassium octoate (0.06%) was dissolved in 100 grams of xylene and added to the reaction mixture. After forty-five minutes, 100% conversion to trimer was achieved. The crosslinker was purified by repeated recrystallization using methyl ethyl ketone and heptane.

EXAMPLE III

A third crosslinker was prepared as follows. Isophorone diisocyanate (3.0 moles) was weighed into a round bottom flask equipped as in Example I and seven drops of dibutyl tin dilaurate catalyst were added. Three moles of 2-ethylhexanol were added dropwise over forty-five minutes. The temperature was held below 50° C. while the flask was flushed with nitrogen. After one hour, 2.0 grams potassium octoate (0.18% on solids) was added and the reaction temperature rose to 80° C. in thirty minutes. An additional 2.4 grams of potassium octoate were added. After one hour at 130° C. an Infrared spectrum showed no NCO peak and the reaction was terminated. The crosslinker was recrystallized from heptane.

EXAMPLE IV

A fourth crosslinker was prepared as follows. Isophorone diisocyanate (3.0 moles) was weighed into a round bottom flask equipped as in Example I and eight drops of dibutyl tin dilaurate were added. Methyl ethyl ketoxime (3.0 moles) was added dropwise over one hour and the temperature was held below 50° C. while flushing with nitrogen. After 30 minutes the NCO conversion was 49.8%. 1.2 grams of potassium octoate (0.13%) was added and the temperature rose to 80° C. over thirty minutes. 3.0 grams of potassium octoate was added and the reaction temperature began to rise. 100 grams of cellosolve acetate was added in order to control the temperature at 120° C. After eight hours the trimer conversion reached 88.75% and would proceed no further. 50 grams of cellosolve acetate and 28 grams methyl ethyl ketoxime were added and then the reaction was terminated. The crosslinker was purified by repeated recrystallization from toluene and heptane.

EXAMPLES V-X

Resin A

A chain extended epoxy ester was prepared by charging into a suitable reactor 1248 parts of Epon 829, 342 parts of Bisphenol A, 463 parts of Emery 1014 Dimer acid and 1400 parts of Soya Fatty Acid. The mixture was heated up to 350° F. at which point an exothermic reaction took place that brought the reaction temperature up to 390° F. After thirty minutes at this temperature, the acid member was measured to be 13.8. After one hour, the acid number was dropped to 5.9. At this point 100 parts of methyl amyl ketone were added and 5 parts of water were distilled off. The resin was then cooled down to 250° F. and 763 parts of methyl amyl ketone were added. The final resin had a Gardner-Hold viscosity of T at 80% solids.

Resin B

Into a suitable reactor were charged 1248 parts of Epon 829, 530 parts of Bisphenol A and 1186 parts of Soya Fatty Acid. The temperature of the mixture was brought up to 350° F. at which point an exothermic reaction took place that raised the temperature up to 380° F. After 30 minutes at this temperature, the acid number was found to be zero. The reaction mixture was then cooled down to 300° F. and 741 parts of methyl amyl ketone were added. The resulting resin had a viscosity of T½ at 80% solids.

Millbase

A composite pigment paste was prepared by grinding in a ballmill the following mixture:

| Composition | Parts by Weight |
| --- | --- |
| Barium Sulfate | 1626 |
| Red Iron Oxide | 60 |
| Titanium dioxide | 105 |
| Silica | 75 |
| Strontium chromate | 99 |
| Wax (EA-1157)[1] | 48 |
| Xylene | 200 |
| Toluene | 240 |
| 2 ethyl hexanol | 57 |
| Resin of Example I | 264 |

[1]Polyethylene was sold by NL Industries of Hightstown, New Jersey.

Primer Coating Compositions

| | Example | | | | | |
| Composition | V | VI | VII | VIII | IX | X |
| --- | --- | --- | --- | --- | --- | --- |
| Resin A | 80 | 80 | 80 | 80 | | |
| Resin B | | | | | 80 | 80 |
| Crosslinker of Ex. I | 40 | | | | | |
| Crosslinker of Ex. II | | 40 | | | 40 | |
| Crosslinker of Ex. III | | | 40 | | | |
| Crosslinker of Ex. IV | | | | 40 | | 40 |
| Millbase | 270 | 270 | 270 | 270 | 270 | 270 |
| Methyl amyl ketone | 70 | 70 | 70 | 70 | 70 | 70 |
| Dibutyl tin dilaurate | 0.6 | 0.6 | 0.6 | 0.6 | 0.6 | 0.6 |
| Curing temp. (°F.) × 30 min. | 360 | 320 | 380 | 340 | 320 | 340 |

All the above formulations gave smooth, hard films that had good solvent resistance and gave good corrosion protection when they were applied over PTQ phosphated steel.

EXAMPLE XI 634 parts of Epon 101 (75% NV in xylene) and 130 parts of PCP-0200[1] were charged into a suitable reactor. The mixture was heated up to 350° F. and 140 parts of xylene were distilled off under vacuum. The batch was cooled down to 260° F. and 1.1 part of dimethyl benzyl amine was added. The batch was kept at 260° F. for 3 hours for chain extension and then cooled down to 200° F. at which point 30 parts of N-methyl ethanol amine and 36.7 parts (70% solution in methyl isobutyl ketone) of methyl isobutyl diketimine of diethylene triamine were added. The batch was kept at 250° F. for one hour and 83 parts of hexyl cellosolve, 8.3 parts of dibutyl tin dilaurate and 287 parts of the crosslinker of Example II (dissolved in 150 parts of ethyl cellosolve) were added. The batch was subsequently dispersed in a solution containing 100 parts water, 22 parts acetic acid, 6 parts Surfnyol 104 and 6 parts Geigy Amine C. An electrodeposition bath was prepared by diluting 250 parts of the active resin with 960 parts of water. Phosphated steel panels were coated at 225 volts for two minutes and yielded smooth, hard, effective films of approximately 0.5-0.6 mil thickness when cured for 20 minutes at 180° C.

[1]PCP-0200 is a polycaprolactone diol sold by Union Carbide.

EXAMPLE XII 481 parts of Epon 829, 130 parts of Bisphenol A and 191 parts of Empol 1016 which is a dimer acid with acid value of 193 available from Emery Inc. were charged into a suitable reactor. The mixture was heated to 330° F. at which point an exothermic reaction took place that brought the temperature up to 400° F. The batch was cooled to 350° F. and kept at this temperature for one hour. The batch was then cooled to 200° F. and 34 parts of N-methyl ethanol amine and 51 parts of methyl isobutyl diketimine of diethylene triamine (70% solution in methyl isobutyl ketone) were added. The batch was kept at 250° F. for one hour and 83 parts of hexyl cellosolve, 10 parts of dibutyl tin dilaurate and 360 parts of crosslinker of Example I (dissolved in 200 parts of ethyl cellosolve) were added. The batch was subsequently dispersed in a solution containing 1200 parts of water, 20 parts of acetic acid, 6 parts of Surfynol 104 and 6 parts of Geigy Amine C to produce a water in oil dispersion. 250 parts of this dispersion were inverted with 500 parts of water in order to prepare an electrodeposition bath. Phosphated steel panels were coated at 225 volts for 2 minutes and yielded smooth, hard flexible films of approximately 0.5-0.6 mils thickness when cured for 20 minutes at 180° C.

In view of the disclosure, many modifications will be apparent to those skilled in the art. It is intended that all such modifications which fall within the true scope of this invention be included within the terms of the appended claims.

What is claimed is:

1. A process for manufacturing pure trifunctional blocked isocyanate compound containing an isocyanurate ring and having the formula

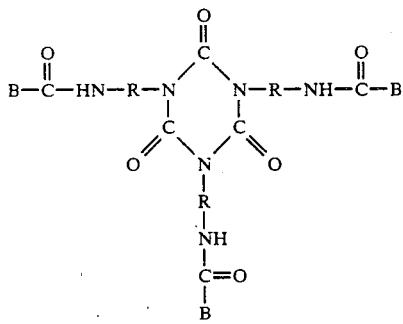

wherein R is selected from the group consisting of aliphatic, cycloaliphatic and aromatic groups and combinations thereof and B is the residue of an active hydrogen containing blocking agent, said process comprising:
(A) reacting (i) organic diisocyanate represented by the formula

OCN—R—NCO and wherein one of the isocyanate groups thereof is more reactive than the other and (ii) sufficient active hydrogen containing blocking agent represented by the formula BH to react substantially all of said more reactive isocyanate groups; and
(B) cotrimerizing the reaction product of (A) in the presence of a catalyst such that said isocyanurate ring containing compound is formed by reaction of 3 moles of said blocked diisocyanate.

2. A process in accordance with claim 1 wherein R is an aromatic group.

3. A process in accordance with claim 1 wherein R is a cycloaliphatic group.

4. A process in accordance with claim 1 wherein R is an aliphatic group.

5. A process in accordance with claim 1 wherein said active hydrogen containing blocking agent employed in preparation of said pure trifunctional blocked isocyanate is selected from the group consisting of (i) aliphatic, cycloaliphatic and aromatic alkyl monoalcohols, (ii) hydroxy amines, (iii) oximes, (iv) lactams and (v) triazoles.

6. A process in accordance with claim 1 wherein said organic diisocyanate used in the preparation of said pure trifunctional blocked isocyanate is selected from the group consisting of: 1-isocyanate-1(p-phenyl isocyanato)methane; 1-isocyanate-2(p-phenyl isocyanato)ethane; 4,4'-diisocyanato-2-nitro-biphenyl; and compounds having the formulas

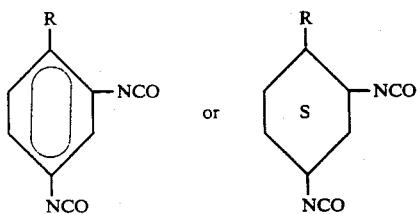

wherein R is selected from the group consisting of methyl, ethyl, t-butyl, chloro, bromomethyl, ethoxy, iso-butoxy, isopropyl, trichloromethyl and methoxy.

7. A process in accordance with claim 6 wherein said active hydrogen containing blocking agent employed in preparation of said pure trifunctional blocked isocyanate is selected from the group consisting of (i) aliphatic, cycloaliphatic and aromatic alkyl monoalcohols, (ii) hydroxy amines, (iii) oximes, (iv) lactams and (v) triazoles.

8. A process in accordance with claim 1 wherein said organic diisocyanate employed in the preparation of said pure trifunctional blocked isocyanate is toluene diisocyanate.

9. A process in accordance with claim 8 wherein said active hydrogen containing blocking agent employed in the preparation of said pure trifunctional blocked isocyanate is methyl ethyl ketoxime.

10. A process in accordance with claim 8 wherein said active hydrogen containing blocking agent employed in the preparation of said pure trifunctional blocked isocyanate is 2-ethylhexanol.

11. A process in accordance with claim 1 wherein said organic diisocyanate employed in the preparation of said pure trifunctional blocked isocyanate is isophorone diisocyanate.

12. A process in accordance with claim 11 wherein said active hydrogen containing blocking agent employed in the preparation of said pure trifunctional blocked isocyanate is methyl ethyl ketoxime.

13. A process in accordance with claim 11 wherein said active hydrogen containing blocking agent employed in the preparation of said pure trifunctional blocked isocyanate is 2-ethylhexanol.

* * * * *